United States Patent
Vinci

(12) 
(10) Patent No.: US 6,630,068 B1
(45) Date of Patent: Oct. 7, 2003

(54) FILTRATION UNIT FOR A DIALYSIS MACHINE

(75) Inventor: Luca Vinci, Poggio Rusco (IT)

(73) Assignee: Hospal AG, Basel (CH)

( * ) Notice: Subject to any disclaimer, the term of this patent is extended or adjusted under 35 U.S.C. 154(b) by 247 days.

(21) Appl. No.: 09/806,297

(22) PCT Filed: Jul. 27, 2000

(86) PCT No.: PCT/IB00/01062

§ 371 (c)(1),
(2), (4) Date: Aug. 13, 2001

(87) PCT Pub. No.: WO01/08722

PCT Pub. Date: Feb. 8, 2001

(30) Foreign Application Priority Data

Jul. 30, 1999 (IT) ...................................... TO99U0148 U

(51) Int. Cl.[7] ........................... B01D 65/00; B01D 61/30
(52) U.S. Cl. ......................... 210/240; 210/232; 210/237
(58) Field of Search ................................ 210/232, 239, 210/237, 240; 248/274.1, 295.11, 309.1, 560, 575, 576

(56) References Cited

U.S. PATENT DOCUMENTS

| | | | |
|---|---|---|---|
| 4,211,380 A | 7/1980 | Lillegard et al. | 248/229 |
| 5,397,462 A | 3/1995 | Higashijima et al. | 210/136 |
| 5,641,144 A | 6/1997 | Hendrickson et al. | 248/292.13 |
| 6,277,277 B1 | 8/2001 | Jacobi et al. | 210/240 |

FOREIGN PATENT DOCUMENTS

| | | |
|---|---|---|
| DE | 93 05 024.0 | 1/1994 |
| EP | 0 887 100 | 12/1998 |
| EP | 1 057 493 A2 | 12/2000 |

*Primary Examiner*—John Kim
(74) *Attorney, Agent, or Firm*—Finnegan, Henderson, Farabow, Garrett & Dunner, L.L.P.

(57) ABSTRACT

A filtration unit is disclosed for a dialysis machine. The unit includes a casing with a number of first connecting elements and a support provided with a number of second connecting elements. Structure is provided for locking the filter on the support when the first and second connecting elements engage each other. The lock structure may include a pair of slides movable between a locking position, in which locking parts interact with stopping portions, and a release position, in which the filter is not locked to the support. An elastic structure may be provided for resiliently urging the slides into the locking position.

17 Claims, 3 Drawing Sheets

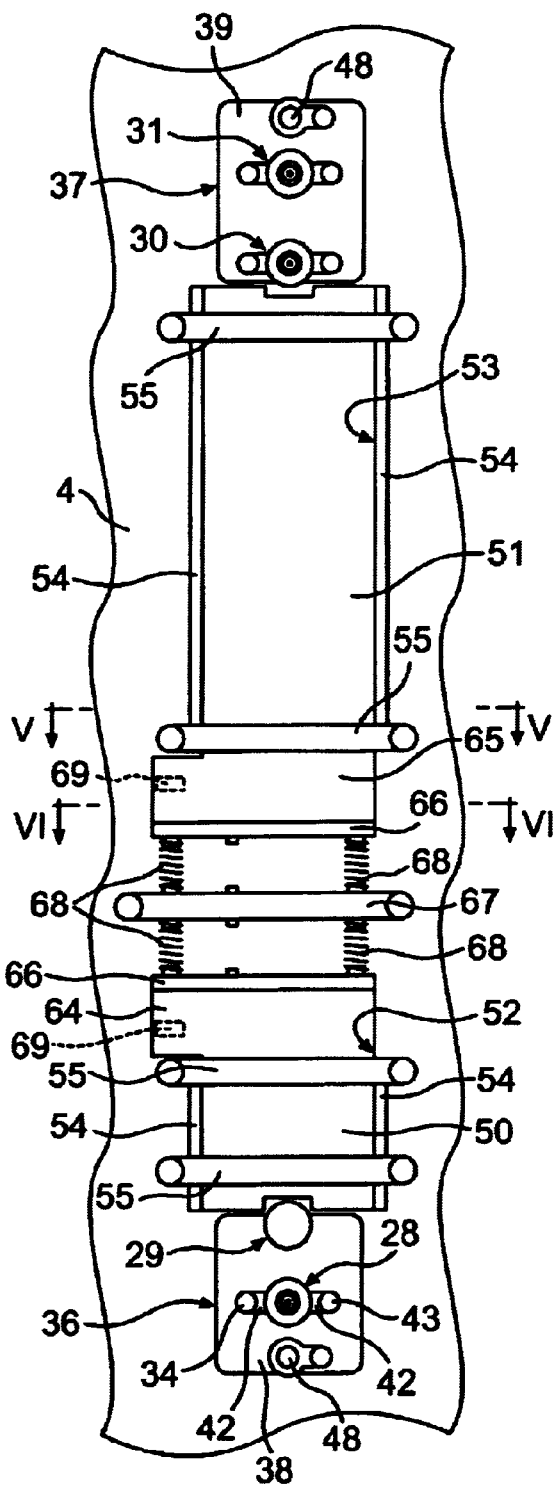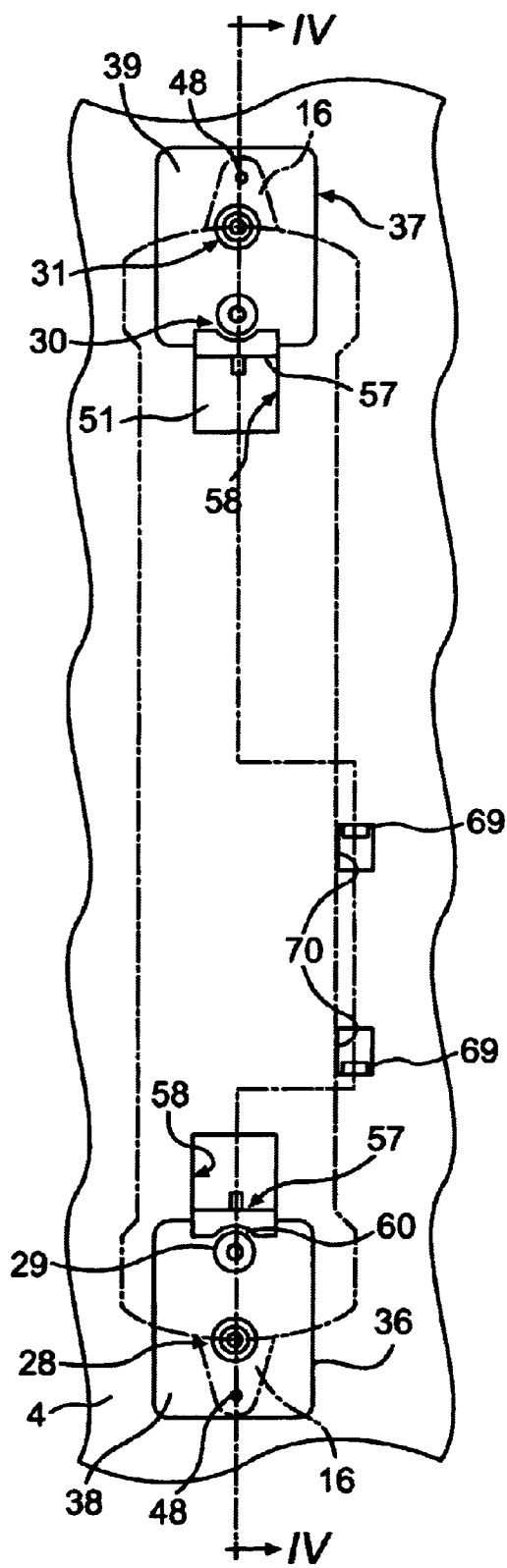
FIG. 3  FIG. 2

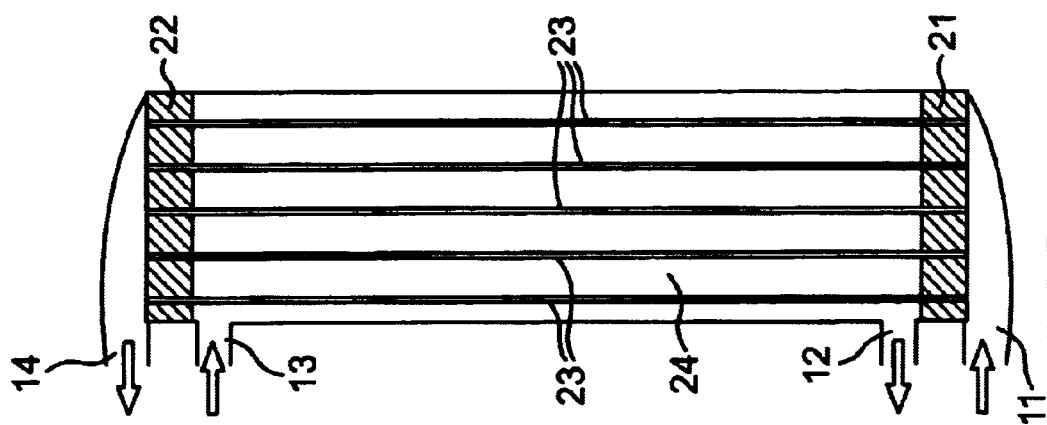
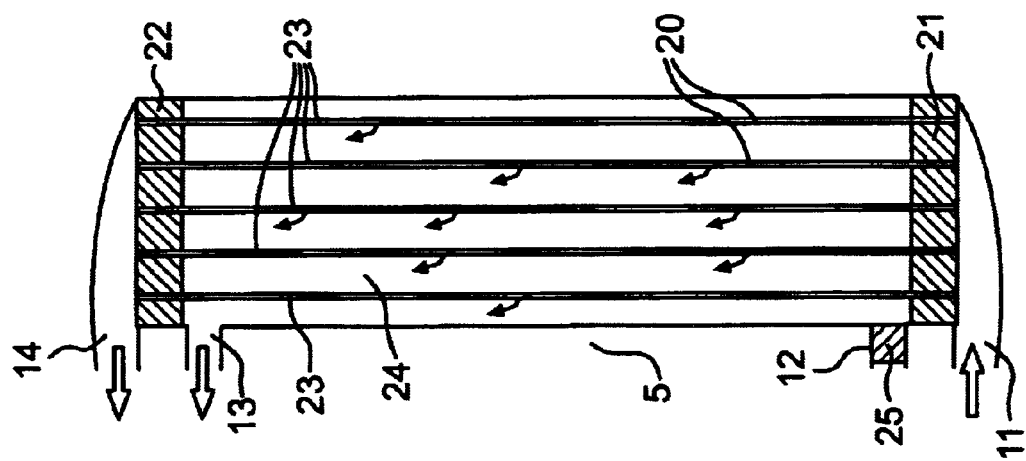
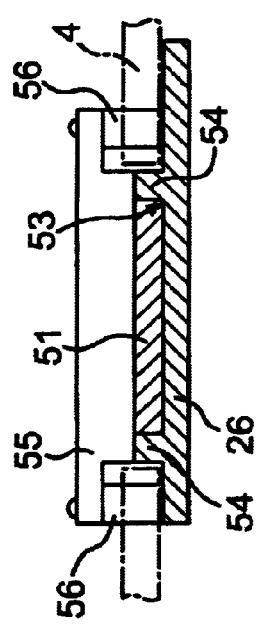
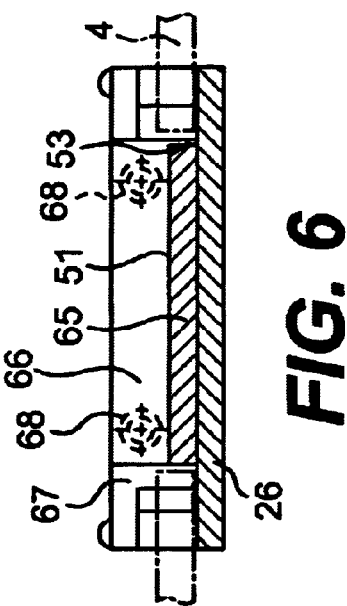

FILTRATION UNIT FOR A DIALYSIS MACHINE

This application is a 371 of PCT/IB00/01062 filed Jul. 27, 2000.

The present innovation relates to a filtration unit for a dialysis machine.

Filtration units are known that comprise a filter, for example an ultrafilter or a dialysis filter, provided with connecting elements, and a support for the filter that can be fixed to a panel of the dialysis machine or to the dialysis machine itself and provided with complementary connecting elements capable of interacting with the connecting elements of the filter when the latter is mounted on the support.

More particularly, filters are known that comprise an elongated hollow casing provided with two flow chambers separated from one another by a porous membrane and provided with two or more tubular connecting elements all arranged on the same side of the casing and possessing axes orthogonal to the axis of the said casing. The membrane can be made up of a bundle of hollow fibres, in which case the flow chambers are defined respectively by the totality of cavities of the fibres and by the volume external to the said fibres.

The support is provided with at least two complementary connecting elements that can interact telescopically with the tubular connecting elements of the filter, and with a device for locking the filter on the support in an operating position in which the tubular connecting elements and the complementary connecting elements are in mutual engagement.

The known units of the type briefly described make it possible to avoid the use of auxiliary ducts for connecting the filter to the machine.

In the known solutions, however, the locking devices are usually rather complex and expensive. In this sector, moreover, there is a demand for making the operations of filter replacement as simple and rapid as possible.

The object of the present innovation is the realization of a filtration unit that makes it possible to solve the problems connected with the known units and to simplify the operations of filter replacement to the maximum possible extent.

The said object is achieved by a filtration unit according to an aspect of the invention.

The present innovation also relates to a support for a filter of a dialysis machine according to an aspect of the invention.

For better understanding of the present innovation, a preferred embodiment is described below, as a non limitative example and with reference to the appended drawings, in which:

FIG. 2 is a front view, with parts removed for clarity, of the unit in FIG. 1;

FIG. 3 is a rear view of the unit in FIG. 1;

FIG. 5 is a section at line V—V in FIG. 3;

FIG. 6 is a section at line VI—VI in FIG. 3;

FIG. 7 is a schematic longitudinal section of a first embodiment of a filter of the unit in FIG. 1; and FIG. 8 is a schematic section of a second embodiment of a filter according to a variant of realization of the present innovation.

Figure 1:
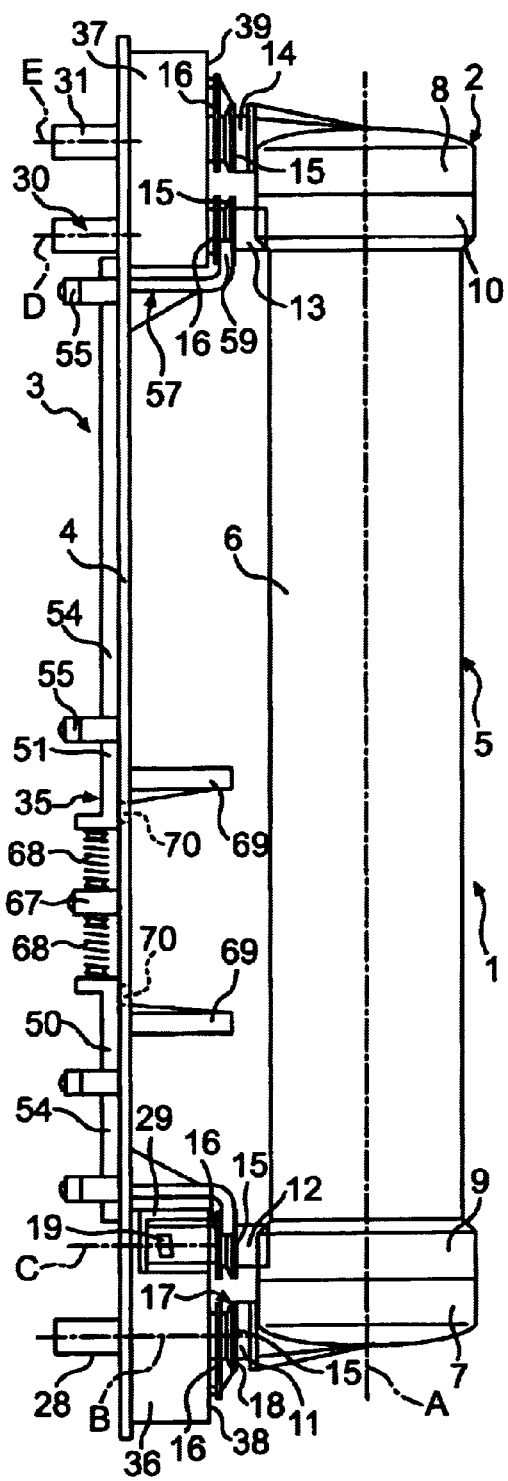
FIG. 1 is a side view of a filtration unit for a dialysis machine constructed according to the present invention.
Figure 4:
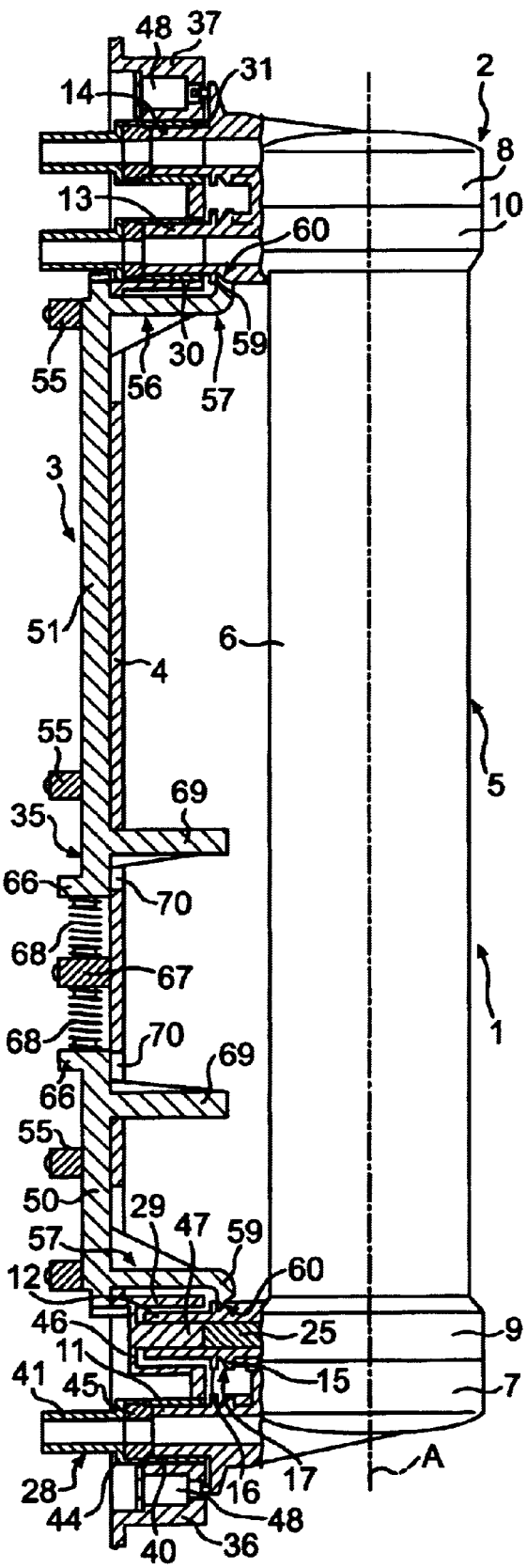
FIG. 4 is a section at line IV—IV in FIG. 2.

Referring to FIGS. 1 and 4, a complete filtration unit for a dialysis machine is denoted by 1.

Unit 1 comprises essentially a filter 2, for example an ultrafilter for a dialysis fluid, and a support 3 that can be fixed, in use, to one wall 4 (FIG. 2) of the dialysis machine.

Filter 2 comprises an elongated casing 5, with axis A, formed by a substantially cylindrical tubular jacket 6 and a pair of caps 7, 8 tightly fitted on opposite axial ends 9, 10, radially expanded, of jacket 6.

Casing 5 has four tubular connecting elements, designated respectively with the numbers 11, 12, 13 and 14. Elements 11 and 14 extend radially from the respective caps 7, 8 of the casing; elements 12 and 13 extend radially from the respective ends 9, 10 of jacket 6 of casing 5. All the connecting elements 11–14 are arranged on a single side of casing 5, and their respective axes B, C, D and E are mutually coplanar and are orthogonal to axis A.

Each of the connecting elements 11–14 is provided with a pair of annular flanges 15, 16 in relief, forming between them a circumferential groove 17. Flanges 15, closer to casing 5, have a chamfer 18 on one of their edges facing the respective flanges 16. Flanges 16, of connecting elements 11 and 14 only, have an elongated shape on opposite sides (FIG. 2).

Finally, connecting element 12 has a pair of radial projections 19 for polarization, diametrically opposite, only one of which is visible in FIG. 1.

Casing 5 (FIG. 7) houses a bundle of hollow fibres 20, of a known type, made of a porous polymeric material; fibres 20, only some of which are illustrated diagrammatically in FIG. 5, are embedded tightly, near their axial ends, in respective heads 21, 22 of synthetic material tightly fitting between connecting elements 11, 12 and, respectively, 13, 14. As a result, two flow chambers 23, 24 are defined, consisting respectively of all of the cavities of the fibres and of the internal volume of casing 5 not occupied by the fibres; flow chambers 23, 24 are separated from each other by a porous membrane defined by the said fibres 20, and communicate respectively with connecting elements 11, 14 and 12, 13.

In the case where filter 2 is used as an ultrafilter for a dialysis fluid, as shown diagrammatically in FIG. 7, connecting element 12 can be closed by a plug 25; connecting element 11 constitutes the inlet for the fluid, which passes from chamber 23 to chamber 24 through the porous membrane, and connecting element 13 constitutes the outlet of the ultrafiltered fluid. Connecting element 14, normally closed in use by a valve (not shown) which is a component part of the machine, constitutes an auxiliary outlet for so-called tangential flow, i.e. for a pulsating flow for filter cleaning sent by the machine and able to flush, from the inside, the membrane constituting the fibres 20 and to drive, towards outlet 14, the particles retained by the said membrane.

Referring to FIGS. 2 and 3, support 3 is fixed to a wall 4 of the machine and carries connecting elements 28, 29, 30, 31 that are complementary and coaxial, in use, to elements 11–14, as well as a locking device 35 that can interact with filter 2 to hold it in an operating position in which connecting elements 11–14 are paired with the complementary connecting elements 28–31.

More particularly, wall 4 has, near its opposite ends, two projections 36, 37 formed as a hollow box, of parallelepipedal shape, delimited at the front by respective flat walls 38, 39.

Projection 36 houses connecting elements 28 and 29. Projection 37 houses connecting elements 30, 31, which are identical to connecting element 28; the description that follows is therefore also valid, mutatis mutandis, for connecting elements 30, 31.

Element 28 comprises a connector that is joined in a releasable manner to wall 38 and includes a bushing formed by two tubular portions 40, 41, which have a larger and a smaller diameter, respectively. A free end of portion 40 engages a hole in wall 38, continuous with the said wall; portion 40 has a pair of radial projections 42 (FIG. 3) which bear against wall 38 and are fixed to it by means of screws 43 (FIG. 3); portion 41 extends beyond wall 4 at the rear, and can be connected to a pipeline of the machine. Portions 40, 41 form an internal shoulder 44, against which an annular cylindrical seal 45 is housed, having an inside diameter substantially equal to the inside diameter of portion 41 and of connecting element 11.

Connecting element 29 is integral with wall 38 and consists of a blind bushing that is able to house connecting element 12 of filter 2. A pin 47, able to engage connecting element 12 of filter 2, extends at the front from a top wall 46 of connecting element 29.

The inside diameter of connecting element 29 is greater than that of portions 40 of connecting elements 28, 30, 31, so as to be able to accommodate the polarization projections 19 of connecting element 12.

Finally, projections 36, 37 house, close to their opposite ends, respective microswitches 48 which can be connected to a control circuit (not shown) of the machine and can be actuated by flanges 16 of connecting elements 11 and 14 when filter 2 is mounted on support 3.

Locking device 35 essentially comprises a pair of slides 50, 51 which can move in a common direction parallel to axis A (and therefore orthogonal to axes B–E of connecting elements 28–31 and parallel to the plane containing them), along respective guides 52, 53 provided on wall 4 between projections 36, 37.

Guides 52, 53 (FIGS. 3 and 5) consist of respective pairs of ribs 54 projecting from wall 4, which guide slides 50, 51 laterally, and a number of transverse bridging elements 55, the ends of which are fixed to respective pairs of pegs 56 extending beyond wall 4 and constrain slides 50, 51 to run in contact with the latter, between ribs 54 (FIG. 5).

Slides 50, 51 have, at their opposite ends, respective integral locking parts 57 which extend beyond and across respective openings 58 in wall 4 (FIG. 2). Locking parts 57 have respective end portions 59 bent to an L shape (FIG. 1) on the respective projections 36, 37 and with respective concave free edges 60, delimited at the front by a conical surface. In section (FIG. 4), edges 60 of portions 59 have a sawtooth profile that is complementary to that of grooves 17, and are able to engage radially with grooves 17 of connecting elements 12, 13 of filter 2 so as to interact with flanges 16 to prevent unthreading of connecting elements 11–14.

As shown in FIG. 3, slides 50, 51 are provided with respective end portions 64, 65 opposite to the locking parts 57, which are of greater width and end in respective edges 66 bent to 90° and opposite a fixed raised element 67, which extends transversely relative to wall 4 and is fixed at the respective ends to pegs 67a projecting from the said wall.

Respective pairs of springs 68 are interposed between the raised element 67 and the edges 66 of slides 50, 51, the said springs being prestressed so as to exert, on slides 50, 51, respective forces that tend to keep the locking parts 57 in engagement with the connecting elements 12, 13 of filter 2.

Referring to FIG. 4, slides 50, 51 are finally provided with respective control levers 69 extending beyond the respective end portions 64, 65 in a direction that is substantially orthogonal to the direction of motion of the said slides across respective openings 70 in wall 4. Levers 69 are parallel and close together, so that they can be actuated with just one hand, in particular between two fingers, to displace slides 50, 51 against the action of springs 68.

In the absence of filter 2, the contact between levers 69 and the respective edges of openings 70 in wall 4 defines the stop position of slides 50, 51.

Levers 69 are advantageously arranged on one side of slides 50, 51 so as to extend beyond the dimensions of filter 2 and therefore to be easily accessible when the filter is fitted (FIG. 2).

Unit 1 operates in the following way.

To mount filter 2 on support 3 it is sufficient to act manually on the control levers 69 of slides 50, 51, in particular bringing them closer together against the action of springs 68. In this manner, slides 50, 51 run towards each other and the locking parts 57 move back, permitting insertion of connecting elements 11–14 in the respective complementary connecting elements 28–31. On releasing the control levers 69, springs 68 return slides 50, 51 to the locking position, in which the locking parts 57 interact with the respective engaging elements 12, 13. In particular, the edges 60 of portions 59 of the locking parts 57 engage the grooves 17 of connecting elements 12, 13 of filter 2, locking filter 2 in the operating position. Manual actuation of slides 50, 51 is not strictly necessary at the stage of installation of filter 2, because pushing in of the said filter produces a force on slides 50, 51 that tends to make them move back on account of the conical profile of the aforementioned edges 60; however, such actuation is preferable for the purpose of avoiding undesirable loads on the locking parts 57 and consequent wear and risks of breakage.

It should be noted that in the operating position of the filter there is top contact between the connecting elements 11, 13, 14 and the seals 45; the channels defined by the aforementioned connecting elements, by the relevant seals 45 and by portions 41 of the relevant connecting elements 28, 30 and 31 are therefore substantially continuous, with constant cross section, and do not have recesses in which the liquid being treated might stagnate, with consequent problems in connection with the cleaning of unit 1.

Mounting of filter 2 in the upside-down position is prevented by the fact that connecting element 12, owing to the presence of projections 19, has a larger transverse dimension than the connecting element 30 of support 3.

When installed, filter 2 acts with flanges 16 of connecting elements 11, 14 on the microswitches 48 (FIG. 4); the machine's control system therefore receives, from each of the microswitches 48, a logic level signal such as to indicate the presence of the filter.

As an alternative to the filter, in the case where ultrafiltration is not necessary, it is possible to fit a bypass device, with which the dialysis machine is nevertheless able to operate. This device (not shown) can be made in such a way that it reproduces the geometry of the casing of filter 2, at least in relation to the parts intended to connect with support 3, but to interact only with one of the two microswitches 48. In this way, the machine's control system is able to discriminate between different operating conditions (presence of a filter, presence of a bypass device) and to detect the possible absence of the filter and of the bypass device, with consequent warning signals and prevention of operation of the machine.

To remove filter 2, it is sufficient to act manually on control levers 69 of slides 50, 51, as described earlier, so as to release the connecting elements 12, 13.

Examination of the characteristics of unit 1 and especially of support 3 constructed according to the present innovation shows the advantages that this provides.

The locking device 35 employing two slides 50, 51 loaded by elastic means and acting transversely on connecting elements 12, 13 makes it possible to effect the operations of installation and removal of filter 2 on support 3 easily and quickly. This device is moreover simple and economical to make.

Realization of the connections by means of front seals makes it possible to avoid stagnation of liquid and to optimize cleaning of the unit.

Finally, connecting elements 28 to 31 are constructed so that they are removable relative to wall 4 and can easily be replaced if there is loss of tightness, without recourse to long and burdensome operations of replacement of the seals.

Finally, it is clear that modifications and variations can be made to unit 1 which are still within the scope of protection of the claims.

In particular, filter 2 can consist of a dialysis filter, as well as an ultrafilter. In this case, as shown schematically in FIG. 8, connecting element 12 is operative and the patients blood and a dialysis fluid pass through the two flow chambers 23, 24, in counterflow. Consequently, connecting element 29 of the support can be of entirely analogous design to the elements 28, 30 and 31 described above.

What is claimed is:

1. Filtration unit for a dialysis machine, comprising:
   a filter that has a casing provided with a number of first connecting elements arranged on the same side of the casing with respective axes parallel to one another, and
   a support provided with a number of second connecting elements that can interact with the first connecting elements, and with releasable locking means for locking the filter on the support in an operating position in which the first and second connecting elements are in mutual engagement,
   characterized in that the releasable locking means comprise:
   a pair of slides provided with respective locking parts, the slides being movable in a direction transverse to the axes of the first connecting elements between a locking position in which the locking parts interact with respective stopping portions carried by the respective first connecting elements and a release position in which the filter is not locked to the support, and
   elastic means for resiliently urging the slides in the locking position.

2. Unit according to claim 1, characterized in that the support comprises a supporting wall provided with the second connecting elements and with means for guidance of the slides interposed between the respective second connecting elements and defining a common direction of motion for the slides orthogonal to the axes of the first connecting elements and parallel to a plane containing them.

3. Unit according to claim 2, characterized in that the slides comprise respective control levers that can be actuated manually to move the slides against the action of the elastic means, the control levers extending beyond the respective slides in a direction substantially orthogonal to the direction of motion of the slides, and being brought close together so that they can be actuated with just one hand.

4. Unit according to one of the preceding claims, characterized in that the locking parts extend totally beyond the slides, the stopping portions of the first connecting elements consisting of stopping flanges that can interact with respective free edges of the locking parts.

5. Unit according to claim 4, characterized in that one of the first connecting elements and one of the second connecting elements have a larger transverse dimension, so as to prevent incorrect mounting of the filter on the support.

6. Unit according to claim 1, characterized in that the support comprises a pair of microswitches positioned near the respective second connecting elements, the first connecting elements comprising respective flanges that can interact with the microswitches.

7. Unit according to claim 2, characterized in that each of the second connecting elements includes an annular seal interacting with the corresponding first connecting elements and defining, with the first and second connecting elements, a channel having a substantially constant cross section.

8. Unit according to claim 6, as characterized in that the filter comprises two pairs of the first connecting elements arranged near opposite ends of the filter, the axes of the first connecting elements being in the same plane, the support being provided with four second connecting elements arranged correspondingly, the two first intermediate connecting elements having the stopping flanges, the two first end connecting elements having the flanges for interacting with the microswitches.

9. Support for a filter comprising a casing provided with a number of first connecting elements arranged on the same side of the casing with respective axes parallel to one another, the support being provided with a number of second connecting elements that can interact with the first connecting elements, and with releasable locking means for locking the filter on the support in an operating position in which the first and second connecting elements are in mutual engagement, characterized in that the releasable locking means comprise:
   a pair of slides provided with respective locking parts, the slides being movable in a direction transverse to the axes of the second connecting elements between a locking position in which the locking parts are able to interact with respective stopping portions carried by the respective first connecting elements and a release position, in which the filter is not locked to the support, and
   elastic means for resiliently urging the slides in the locking position.

10. Support according to claim 9, characterized in that it comprises a supporting wall provided with the second connecting elements and means of guidance for the slides interposed between the respective second connecting elements and defining a common direction of motion for the slides orthogonal to the axes of the second connecting elements and parallel to a plane containing them.

11. Support according to claim 10, characterized in that the slides comprise respective control levers that can be actuated manually to move the slides against the action of the elastic means, the control levers extending beyond the respective slides in a direction substantially orthogonal to the direction of motion of the slides, and being close together so that they can be actuated with just one hand.

12. Support according to claim 11, characterized in that it comprises a raised element fixed to the supporting wall and interposed between the slides, the elastic means comprising springs compressed between the raised element and each of the slides.

13. Support according to claim 10, characterized in that the means of guidance comprise respective pairs of projections of the supporting wall interacting laterally with the respective slides, and transverse bridging elements constraining the slides to run in contact with the supporting wall.

14. Support according to claim 9, as characterized in that the locking parts extend totally beyond the slides and have respective free edges that can interact radially with the stopping portions of the first connecting elements of the filter.

15. Support according to claim 9, characterized in that it comprises a pair of microswitches positioned near the respective second connecting elements, and capable of being actuated by respective flanges of the first connecting elements.

16. Support according to claim 10, characterized in that the second connecting elements are mounted removably on the supporting wall.

17. Support according to claim 10, characterized in that the second connecting elements comprise respective annular seals that can interact at the top with respective first connecting elements of the filter.

* * * * *